(12) United States Patent
Kumar et al.

(10) Patent No.: US 7,414,143 B2
(45) Date of Patent: **\*Aug. 19, 2008**

(54) PROCESS FOR THE PREPARATION OF 4,4-DIMETHYL-6-ETHYNYLTHIOCHROMAN

(75) Inventors: Bobba Venkata Siva Kumar, Mumbai (IN); Vishvas Dattatraya Patil, Ahmedabad (IN); Changdev Namdev Raut, Navi Mumbai (IN); Shekhar Bhaskar Bhirud, Navi Mumbai (IN); Batchu Chandrasekhar, Navi Mumbai (IN)

(73) Assignee: Glenmark Pharmaceuticals Limited, Mumbai (IN)

( * ) Notice: Subject to any disclaimer, the term of this patent is extended or adjusted under 35 U.S.C. 154(b) by 393 days.

This patent is subject to a terminal disclaimer.

(21) Appl. No.: 11/158,856

(22) Filed: Jun. 22, 2005

(65) Prior Publication Data

US 2005/0240029 A1 Oct. 27, 2005

Related U.S. Application Data

(63) Continuation of application No. 10/883,880, filed on Jul. 2, 2004, now Pat. No. 6,963,002.

(60) Provisional application No. 60/580,494, filed on Jun. 17, 2004.

(30) Foreign Application Priority Data

Jul. 4, 2003 (IN) .................................. 685/2003

(51) Int. Cl.
*C07D 335/04* (2006.01)
(52) U.S. Cl. ...................................................... 549/23
(58) Field of Classification Search .................... 549/23
See application file for complete search history.

(56) References Cited

U.S. PATENT DOCUMENTS 5,717,094 A  2/1998  Chandraratna
5,917,082 A * 6/1999  Vuligonda et al. .......... 560/100

FOREIGN PATENT DOCUMENTS

| EP | 0 290 130 | 11/1988 |
| EP | 0 419 132 | 3/1991 |
| WO | WO 93/16068 | 8/1993 |
| WO | WO 96/11686 | 4/1996 |

OTHER PUBLICATIONS

Johnson et al. "Synthesis and Biological Activity of High-Affinity Retinoic Acid Receptor Antagonists", *Bioorganic & Medicinal Chemistry*, Elsevier Science Ltd., (7):1321-1338, Jul. 1999.

\* cited by examiner

*Primary Examiner*—Rebecca L Anderson
*Assistant Examiner*—Robert Havlin
(74) *Attorney, Agent, or Firm*—M. Carmen & Associates, PLLC

(57) ABSTRACT

An improved process for the preparation of key intermediates for tazarotene, 4,4-dimethyl-6-ethynylthiochroman, is provided comprising (a) reacting 4,4-dimethyl-6-acetylthiochroman of the formula

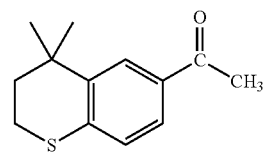

with an acid chloride and an amido-group containing compound of the general formula

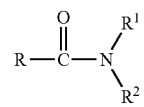

wherein R is hydrogen or a hydrocarbyl of from 1 to 15 carbon atoms and $R^1$ and $R^2$ can be the same or different and are hydrocarbyls of from 1 to 15 carbon atoms or $R^1$ and $R^2$ together with the nitrogen atom to which they are bonded are joined together to form a heterocyclic group, optionally containing one or more additional heterocyclic atoms, or one of $R^1$ and $R^2$ together with the nitrogen atom to which it bonded are joined together with the carbonyl radical to form a heterocyclic group, optionally containing one or more additional heterocyclic atoms to form a β-chloro vinyl carbonyl compound intermediate of the general formula

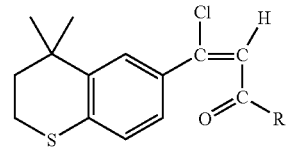

wherein R has the aforestated meanings; and (b) reacting the β-chloro vinyl carbonyl compound intermediate with an alkali metal to provide the 4,4-dimethyl-6-ethynylthiochroman.

20 Claims, No Drawings

PROCESS FOR THE PREPARATION OF 4,4-DIMETHYL-6-ETHYNYLTHIOCHROMAN

CLAIM FOR PRIORITY

This application is a continuation of U.S. patent application Ser. No. 10/883,880, filed Jul. 2, 2004, now U.S. Pat. No. 6,963,002 which claims priority to U.S. Provisional Application No. 60/580,494, filed Jun. 17, 2004, and Indian Provisional Application No. 685/MUM/2003, filed Jul. 4, 2003, the contents of each of which are incorporated herein by reference in their entireties.

BACKGROUND OF THE INVENTION

1. Technical Field

The present invention generally relates to an improved process for the preparation of intermediates for tazarotene. More specifically, the present invention relates to an improved process for the preparation of the intermediate 4,4-dimethyl-6-ethynylthiochroman using a Vilsmeier Haack reaction.

2. Description of the Related Art

The present invention is directed towards an improved process for the preparation of intermediates of tazarotene (also known as ethyl-6-[2-(4,4-dimethylthiochroman-6-yl)-ethynyl]) of Formula I:

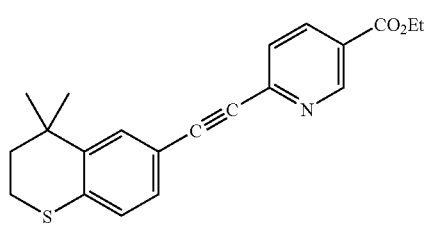

Tazarotene is a member of the acetylenic class of retinoids and is a prodrug that is converted to its active drug form, known as AGN 190299, in most biological systems by rapid deesterificaion of the cognate carboxylic acid of tazarotene. AGN 190299 binds to all three members of the retinoic acid receptor (RAR) family: RARα, RARβ, RARγ. AGN 190299 shows relative selectivity for the RARβ and RARγ and may modify gene expression. Tazarotene is used in the treatment of psoriasis and is commercially available under the trade name Tazorac®.

A key intermediate in the preparation of tazarotene, 4,4-dimethyl-6-ethynylthiochroman (II), is prepared as shown in Scheme I:

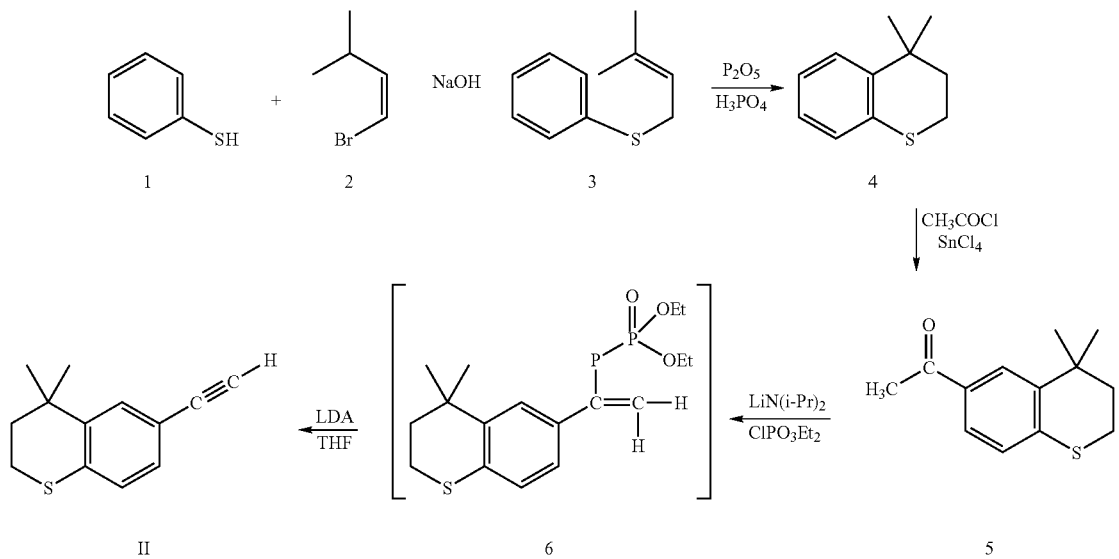

Thiophenol (1) and 1-bromo-3-methyl-2-butene (2) are heated at reflux with sodium hydroxide in acetone resulting in phenyl-3-methylbut-2-enylsulfide (3). The phenyl-3-methylbut-2-enyl sulfide (3) is cyclized by refluxing with phosphorus pentoxide and phosphoric acid in benzene to yield 4,4-dimethylthiochroman (4). The 4,4-dimethylthiochroman (4) is reacted with acetyl chloride catalyzed by tin (IV) chloride (SnCl$_4$) in benzene resulting in 4,4-dimethyl-6-acetylthiochroman (5). The 4,4-dimethyl-6-acetylthiochroman (5) is dehydrated with lithium diisopropylamide (LDA) and diethyl chlorophosphate in tetrahydrofuran (THF) results in the initial 6-ethenyl phosphonate intermediate (6). This intermediate undergoes further reaction with two equivalents of LDA to give 4,4-dimethyl-6-ethynylthiochroman (II).

The main disadvantages of this process include the use of difficult reagents, such as LDA, which is moisture sensitive, expensive, pyrophoric, and difficult to handle on a commercial scale, and diethyl chlorophosphate, which is highly toxic and corrosive. The process is also time consuming and includes low temperatures in an inert atmosphere, which is difficult to achieve on a commercial scale.

Accordingly, there remains a need for an improved process for preparing 4,4-dimethyl-6-ethynylthiochroman that eliminates and reduces the drawbacks of the prior art in a convenient and cost efficient manner on a commercial scale.

SUMMARY OF THE INVENTION

One aspect of the present invention is the preparation of a key intermediate of tazarotene, 4,4-dimethyl-6-ethynylthiochroman, via a Vilsmeier Haack reaction. The Vilsmeier Haack reaction comprises (a) reacting 4,4-dimethyl-6-acetylthiochroman of the formula

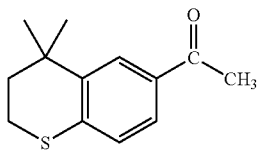

with an acid chloride and an amido-group containing compound of the general formula

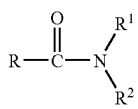

wherein R is hydrogen or a hydrocarbyl of from 1 to about 15 carbon atoms and $R^1$ and $R^2$ can be the same or different and are hydrocarbyls of from 1 to about 15 carbon atoms or $R^1$ and $R^2$ together with the nitrogen atom to which they are bonded are joined together to form a heterocyclic group, optionally containing one or more additional heterocyclic atoms, or one of $R^1$ and $R^2$ together with the nitrogen atom to which it is bonded are joined together with the carbonyl radical to form a heterocyclic group, optionally containing one or more additional heterocyclic atoms to form a β-chloro vinyl carbonyl compound intermediate of the general formula

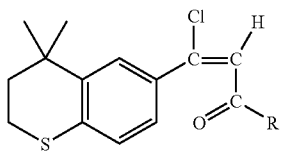

wherein R has the aforestated meanings; and (b) reacting the β-chloro vinyl carbonyl compound intermediate with an alkali metal to provide the 4,4-dimethyl-6-ethynylthiochroman.

The advantages of the present invention include:

1) The process may be performed without the isolation and purification of intermediates after each step. The intermediates of the present invention are advantageously formed in a solvent which can be used in further steps of the synthesis.

2) Avoids the use of low temperatures (e.g., −78° C.) which is expensive to work in on a commercial scale.

3) Avoids the use of difficult reagents such as LDA, benzene, diethyl chlorophosphate and diethyl ether. Each of these reagents presents various hazards which make them particularly difficult to handle when working in commercial quantities.

DETAILED DESCRIPTION OF THE PREFERRED EMBODIMENTS

In one aspect of the process of the present invention, 4,4-dimethyl-6-ethynylthiochroman can be prepared by a process including at least a Vilsmeier Haack reaction that forms a β-chloro vinyl carbonyl compound intermediate and then reacting the intermediate with an alkali metal to form the 4,4-dimethyl-6-ethynylthiochroman. In a first step of the process of the present invention, 4,4-dimethyl-6-acetylthiochroman of the formula

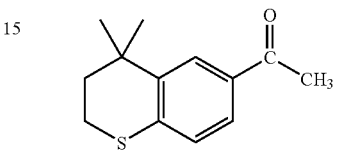

is reacted with an acid chloride and an amido-group containing compound of the general formula

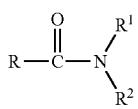

wherein R is hydrogen or a hydrocarbyl of from 1 to about 15 carbon atoms, preferably from 1 to about 12 carbon atoms and more preferably from 1 to 6 carbon atoms including, by way of illustration, unsubstituted straight or branched aliphatic, cycloaliphatic and aromatic groups and cycloaliphatic and aromatic groups substituted with one or more straight or branched aliphatic, cycloaliphatic and/or aromatic groups. Thus, for example, R may be hydrogen, an alkyl group of 1 to about 6 carbon atoms or a phenyl group. As one skilled in the art will readily appreciate, when R is hydrogen the resulting β-chloro vinyl carbonyl compound intermediate formed in this step will be a β-chloro vinylaldehyde intermediate and when R is a hydrocarbyl the resulting β-chloro vinyl carbonyl compound intermediate formed in this step will be a β-chloro vinylketone intermediate. $R^1$ and $R^2$ can be the same or different and are hydrocarbyls of from 1 to about 15 carbon atoms, preferably from 1 to about 12 carbon atoms and more preferably from 1 to 6 carbon atoms including, by way of illustration, unsubstituted straight or branched aliphatic, cycloaliphatic and aromatic groups and cycloaliphatic and aromatic groups substituted with one or more straight or branched aliphatic, cycloaliphatic and/or aromatic groups. Alternatively, $R^1$ and $R^2$ together with the nitrogen atom to which they are bonded are joined together to form a heterocyclic group, optionally containing one or more additional heterocyclic atoms (e.g., O, S, N, etc.), for example, cyclic amines such as pyrrolidine, piperidine, piperazine, morpholine and the like. Alternatively, one of $R^1$ and $R^2$ together with the nitrogen atom to which it is bonded are joined together with the carbonyl radical to form a heterocyclic group, optionally containing one or more additional heterocyclic atoms, such as a pyrrolidone and the like. This reaction advantageously forms a Vilsmeier Haack reagent, β-chloro vinyl carbonyl compound intermediate of the general formula

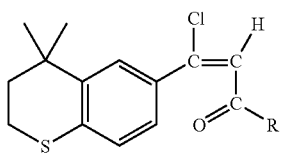

wherein R has the aforestated meanings.

Examples of the foregoing amido-group containing compounds include, but are not limited to, dimethyl formamide, N-methyl formanilide, N-formyl piperidine, N-formyl morpholine, dimethyl acetamide, N-methyl pyrrolidone, N,N-dimethyl benzamide and the like and mixtures thereof with dimethyl formamide being preferred. Generally, the amido-group containing compounds will be present in an amount ranging from about 45 to about 90 wt. percent and preferably from about 55 to about 75 wt. percent, based on the total weight of the reaction mixture.

The acid chlorides for use in the process of the present invention are used to convert formamide derivatives and react with the 4,4-dimethyl-6-ethynylthiochroman to form the β-chloro vinyl carbonyl compound intermediates. Any acid chloride may be used herein including, for example, phosphorous oxychloride ($POCl_3$). In one embodiment of the present invention, the acid chloride is selected from the group consisting of phosphorous oxychloride, thionyl chloride, phosgene and oxalyl chloride. The acid chloride may be present in a ratio of about 1:3 (w/v) to about 1:5 (w/v) with respect to 4,4-dimethyl-6-acetylthiochroman. The acid chloride may be added dropwise to the 4,4-dimethyl-6-acetylthiochroman in the amido-group containing compound over a time period of from about 1 to about 2 hours at a temperature ranging from about –10° C. to about 100° C. After addition of the acid chloride, the reaction time for the Vilsmeier Haack reaction may be about 4 to about 8 hours, and the reaction temperature may range from about –10° C. to about 35° C. When the Vilsmeier Haack reaction of the present invention is carried out at a temperature below about 10° C., the impurity profile is advantageously reduced.

As one skilled in the art will readily appreciate, the foregoing reaction may be carried out in one of two ways: (1) by adding the 4,4-dimethyl-6-acetylthiochroman to the amido-group containing compound and then adding the acid chloride; or (2) by adding the acid chloride to the amido-group containing compound and then adding the 4,4-dimethyl-6-acetylthiochroman.

Following the reaction of the 4,4-dimethyl-6-acetylthiochroman with the amido-group containing compound and acid chloride, it may be desirable to add a suitable solvent to the reaction mixture to extract the desired β-chloro vinyl carbonyl compound intermediate. Useful solvents include, but are not limited to, chlorinated alkane solvents such as dichloromethane, chloroform, carbon tetrachloride and the like and mixtures thereof. The solvent is generally added in an amount of from about 0 to about 30 wt. percent Next, the Vilsmeier Haack reaction product can be reacted with an alkali metal to form the 4,4-dimethyl-6-ethynylthiochroman. Useful alkali metals include, but are not limited to, sodium hydroxide and potassium hydroxide and the like and mixtures thereof. The reaction is ordinarily carried out at a temperature ranging from about 20° C. to about 100° C. Useful alkali metal include, but are not limited to, sodium hydroxide, potassium hydroxide, lithium hydroxide and the like and mixtures thereof. The alkali metal is ordinarily added in a molar ratio of about 1:4 to about 1:8 with respect to the β-chloro vinyl carbonyl compound intermediate. It is particularly advantageous to carry out the reaction in step (b) in an ether type solvent medium. Useful ether type solvents include, but are not limited to, a dialkyl ether wherein the alkyl groups are the same or different and are from 1 to about 12 carbon atoms, e.g., dimethylether, diethylether and di-i-propylether; dioxane; tetrahydrofuran; pyran and mixtures thereof. The solvent will ordinarily be present in an amount ranging from about 1:2 w/v to about 1:30 w/v with respect to the reactants, i.e. for every 1 gram of a reactant, 2 to 30 volume of the ether type solvent may be used. The reaction time will ordinarily range from about 30 minutes to about 18 hours. The reaction mixture may then be quenched with saturated ammonium chloride.

In a preferred embodiment of the process of the present invention, the reaction includes reacting 4,4-dimethyl-6-acetylthiochroman (5) with dimethyl formamide and phosphorous oxychloride to form a Vilsmeier Haack reagent, β-chloro vinylaldehyde (7) and then adding sodium hydroxide to form 4,4-dimethyl-6-ethynylthiochroman (II) as shown in Scheme II:

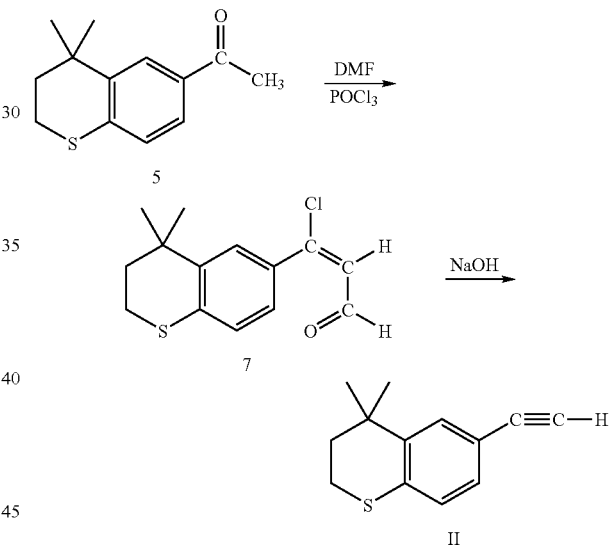

Generally, to prepare the starting material 4,4-dimethyl-6-acetylthiochroman, thiophenol may be reacted with a strong base in about equimolar amounts in ethylene dichloride (EDC) and methanol at reflux. The mixture of methanol and ethylene dichloride (1:1 v/v) may vary from about 1:12 w/v to about 1:15 w/v with respect to the thiophenol. The strong base is preferably an alkali metal hydroxide, such as, for example, sodium hydroxide. 1-Bromo-3-methyl-2-butene is added in about equimolar amounts and the reaction mixture may be refluxed for about 8 to about 12 hours to form phenyl-3-methylbut-2-enyl sulfide.

The phenyl-3-methylbut-2-enyl sulfide is present in the EDC layer and does not need to further purified or separated prior to reacting it with phosphorous pentoxide in the presence of phosphoric acid. The reaction is heated to reflux with stirring for about 8 to about 12 hours. This reaction closes the ring of the sulfide forming 4,4-dimethylthiochroman.

The 4,4-dimethylthiochroman is present in the EDC layer and also does not need to be further purified or separated prior to reacting it with acetyl chloride in the presence of aluminum chloride. The reaction mixture is stirred for about 30 minutes to about 3 hours at a temperature ranging from about −10° C. to about 10° C. The reaction is quenched and the product is 4,4-dimethyl-6-acetylthiochroman which is present in the EDC layer. The product may be used without further purification to perform the Vilsmeier Haack reaction.

The following examples are provided to enable one skilled in the art to practice the invention and are merely illustrative of the invention. The examples should not be read as limiting the scope of the invention as defined in the claims.

EXAMPLE 1

Preparation of 3-[4,4-dimethylthiochroman-6-yl]-3-chloro-2-propene-1-al

In a 500 ml 4-necked round bottom flask fitted with a mechanical stirrer and a reflux condenser, 6-acetyl-4,4-dimethylthio-chroman (22 g) and dimethylformamide (38 ml) are added at a temperature in the range of from about 35° C. to about 95° C. under stirring. The reaction mixture is then cooled to a temperature in the range of from about −5° C. to about 0° C. Phosphorus oxychloride (17.2 g) is added to the reaction mixture dropwise over about 30 minutes. Following the addition of the phosphorous oxychloride, the reaction mixture is maintained at a temperature in the range of from about 10° C. to about 15° C. for about 8 hours to about 10 hours. After completion of the reaction as determined by TLC, the reaction mixture is added to cold water (100 ml) at a temperature of from about 0° C. to about 5° C. containing sodium acetate (25 g). The aqueous layer is extracted with dichloromethane (200 ml×3). The organic layer is washed with demineralized water (100 ml×3) until it becomes neutral.

The dichloromethane layer is concentrated on a rotavapor bath at a temperature in the range of from about 25° C. to about 30° C. under plant vacuum until no more drops are observed. The resulting residual oil is purified by flash chromatography with petroleum ether and ethyl acetate (9:1 mixture) resulting in a pale yellow oil, weighing about 22 g, yield of about 82%, purity of about 98% (HPLC). The IR (neat) shows the following stretching 2900 $cm^{-1}$ (C—H str), 2750 $cm^{-1}$ (C—H str), 1690 $cm^{-1}$ (—C=O str), 1620 $cm^{-1}$ (—C=C-str), 760 $cm^{-1}$ (—C=C—Cl str). The 1H-NMR (CDCl$_3$) using TMS as internal standard shows the following signals at δ 1.35 (6H, s) 1.92-1.98 (2H, m), 3.02-3.08 (2H, m), 5.5 (1H, s), 7.13 (1H, d 8.6 Hz), 7.58 (1H, dd, J 8.6 Hz, 2H), 7.99 (1H, d, J 2 Hz), 8.9 (s, 1H). The CI mass shows m/z 266 (M+).

Preparation of 4,4-dimethyl-6-ethynylthiochroman

In a 250 ml 4-necked round bottom flask fitted with a mechanical stirrer and reflux condenser, water (41.3 ml) and sodium hydroxide (5.22 g, 0.1305M) are added and heated to a temperature in the range of from about 80° C. to about 90° C. The reaction mixture is stirred, and a solution of 3-[4,4-dimethylthiochroman-6-yl]-3-chloro-2-propene-1-al (3.0 gm, 0.0113 M) is added dropwise in 1,4-dioxane (52.2 ml) under vigorous stirring. The reaction mixture is maintained at a temperature in the range of from about 80° C. to about 90° C. for about 2 hours. After completion of the reaction as determined by TLC, the solvents are distilled off and the product is extracted with ether (15 ml×3). The ether layer is washed with brine (15 ml×3). The organic layer is dried over sodium sulfate, and the solvent is distilled off to get an oily residue. The resulting crude oil is distilled under high vacuum and the vapors are collected at a temperature of about 126° C./0.2 mm as the main product. The main fraction appears as red viscous oil, which upon standing crystallized. Net wt of about 2.00 g, yield of about 87.68%; m.p. in the range of from about 69° C. to about 72° C., purity of about 98% (HPLC). The IR (neat) shows the following absorptions: 3200 $cm^{-1}$ (C—H-str), 2950 $cm^{-1}$ (—C=C—H str), 2100 $cm^{-1}$ (—C≡C—). The 1H-NMR (CDCl$_3$), TMS as internal standard shows the following signals δ 1.35 (6H, s), 1.92-1.98 (2H, m), 3.02-3.08 (3H, m), 7.13 (1H, d 8.6 Hz), 7.58 (1H, dd, J 8.6 Hz, 2 Hz), 7.99 (1H, d, J 2 Hz). The CI/MS shows m/z 202 (M+).

EXAMPLE 2

Preparation of phenyl-3-methylbut-2-enyl sulfide

In a 5 L 4-neck round bottom flask, methanol (1400 ml) and thiophenol (200 g) were added under stirring at a temperature ranging from about 25° C. to about 35° C. Sodium hydroxide (powder LR grade) (73.60 g) and methanol (100 ml) were added under stirring. The reaction mixture was left under a nitrogen atmosphere and stirred at room temperature (about 25° C. to about 30° C.) for an hour. 1-bromo-3-methyl-2-butene (274 gm) was added to the reaction mixture and it was observed that the temperature rose to about 40° C. The reaction mixture was heated to reflux and maintained for about 12 hours. After completion of the reaction as determined by HPLC, the methanol was distilled out from reaction mixture under vacuum at a temperature below 60° C. Ethylene dichloride (1500 ml) and water (1000 ml) were added to the residue. The organic layer was separated and washed with a 5% sodium hydroxide (600 ml) solution, and then water (3×600 ml) until the pH was about 7. The organic layer was then washed with a brine solution (700 ml). The ethylene dichloride was distilled out until the moisture content was less than 0.1%.

Preparation of 4,4-dimethylthiochroman

In a 5 L 4-neck round bottom flask, ethylene dichloride (1500 ml) was added to the phenyl-3-methylbut-2-enyl sulfide from the previous step. Phosphorous pentoxide (200 gm) was added to the reaction mixture at a temperature ranging from about 25° C. to about 35° C. under stirring. Ortho phosphoric acid (174 ml) was added carefully under nitrogen. The reaction mixture was heated to reflux, a temperature of about 80° C. to about 90° C. and maintained at that temperature for about 12 hours. After completion of the reaction as determined by HPLC, the reaction mass was cooled to a temperature ranging from about 25° C. to about 35° C. and water (2000 ml) was slowly added to the reaction mass. The organic layer was separated, and the aqueous layer was extracted with EDC (2 L×2). The organic layers were combined and washed with saturated sodium bicarbonate solution (2 L×2) and water (1.5 L×2) until the pH was about 7. This was followed by a washing with a brine solution (1.5 L). The EDC layer was distilled out under reduced pressure below a temperature of about 70° C. until the moisture content was less than 0.1%. EDC (2 L) was added to the residue and taken for the next step without further purification Preparation of 4,4-dimethyl-6-acetylthiochroman In a 5 L 4-neck round bottom flask, EDC (2 L) was added to the 4,4-dimethylthiochroman from the previous step. The contents were stirred and cooled to a temperature of about −10° C. Aluminum chloride (252 g) was slowly added to the reaction mixture. Acetyl chloride (152.7 g) was added at a temperature ranging from about −10° C. to about −5° C. over about 1.5 hours. After the addition, the reaction mixture was maintained at a temperature ranging from about −5° C. to about 0° C. for about 2 hours. The reaction was monitored by TLC. [If the reaction is incomplete as determined by TLC, bring the reaction mixture to a temperature ranging from about 25° C. to about 35° C. under stirring for about 4 hours.] The reaction mixture was quenched with ice (4.87 kg) and hydrochloric acid (1.63 L), and the reaction mass was stirred for about 30 minutes. EDC (2.5 L) was added to the reaction mass. The layers were separated. The aqueous layer was extracted with MDC (2×2 L). The organic layers were combined and washed with 5% sodium bicarbonate solution (2×2 L) and water (2×2 L) until the pH is about 7. This was followed by a washing with brine (1.5 L). The EDC and MDC layer were distilled out under reduced pressure until the moisture content was less than about 0.1%. There was a residual volume of about 3 L.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A β-chloro vinyl carbonyl compound of the general formula:

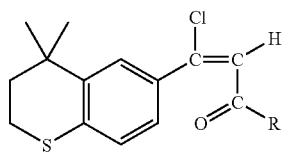

wherein R is hydrogen or a hydrocarbyl of from 1 to about 15 carbon atoms.

2. The β-chloro vinyl carbonyl compound of claim 1, wherein R is hydrogen.

3. The β-chloro vinyl carbonyl compound of claim 1, wherein R is a hydrocarbyl group of 1 to about 15 carbon atoms.

4. The β-chloro vinyl carbonyl compound of claim 1, wherein R is an alkyl group of 1 to 6 carbon atoms.

5. The β-chloro vinyl carbonyl compound of claim 1, wherein R is a phenyl group.

6. The β-chloro vinyl carbonyl compound of claim 1, having a purity of about 98%.

7. A process for the preparation of a β-chloro vinyl carbonyl compound of the general formula I:

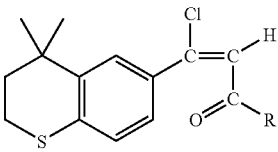

wherein R is hydrogen or a hydrocarbyl of from 1 to about 15 carbon atoms, the process comprising reacting a 4,4-dimethyl-6-acetylthiochroman of the formula II

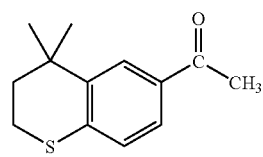

with an acid chloride and an amido-group containing compound of the general formula III

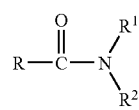

wherein R has the aforestated meanings and $R^1$ and $R^2$ can be the same or different and are hydrocarbyls of from 1 to about 15 carbon atoms or $R^1$ and $R^2$ together with the nitrogen atom to which they are bonded are joined together to form a heterocyclic group, optionally containing one or more additional heterocyclic atoms, or one of $R^1$ and $R^2$ together with the nitrogen atom to which it is bonded are joined together with the carbonyl radical to form a heterocyclic group, optionally containing one or more additional heterocyclic atoms to provide the β-chloro vinyl carbonyl compound of formula I.

8. The process of claim 7, wherein the acid chloride is selected from the group consisting of phosphorous oxychloride, thionyl chloride, phosgene, oxalyl chloride and mixtures thereof.

9. The process of claim 7, wherein the acid chloride is phosphorous oxychloride.

10. The process of claim 7, wherein R is hydrogen and $R^1$ and $R^2$ each are hydrocarbyl groups of 1 to about 15 carbon atoms.

11. The process of claim 7, wherein R is hydrogen and $R^1$ and $R^2$ each are hydrocarbyl groups of 1 to about 12 carbon atoms.

12. The process of claim 7, wherein R is hydrogen and $R^1$ and $R^2$ each are hydrocarbyl groups of 1 to 6 carbon atoms.

13. The process of claim 7, wherein R is hydrogen and $R^1$ and $R^2$ together with the nitrogen atom to which they are bonded are joined together to form a heterocyclic group.

14. The process of claim 7, wherein R is a hydrocarbyl group of from 1 to about 15 carbon atoms and $R^1$ and $R^2$ are independently hydrocarbyl groups of from 1 to about 15 carbon atoms.

15. The process of claim 7, wherein R is a hydrocarbyl of from 1 to about 15 carbon atoms and $R^1$ and $R^2$ together with the nitrogen atom to which they are bonded are joined together to form a heterocyclic group.

16. The process of claim 7, wherein the amido-group containing compound is selected from the group consisting of dimethyl formamide, N-methyl formanilide, N-formyl piperidine, N-formyl morpholine, dimethyl acetamide, N-methyl pyrrolidone, N,N-dimethyl benzamide and mixtures thereof.

17. The process of claim 7, wherein the amido-group containing compound is present in an amount of about 45 to about 90 weight percent, based on the total weight of the reaction mixture.

18. The process of claim 7, wherein the amido-group containing compound is present in an amount of about 55 to about 75 weight percent, based on the total weight of the reaction mixture.

19. The process of claim 7, wherein the acid chloride is present in a ratio of about 1:3 (w/v) to about 1:5 (w/v) with respect to the 4,4-dimethyl-6-acetylthiochroman.

20. The process of claim 7, wherein the acid chloride is phosphorous oxychloride and the amido-group containing compound is dimethyl formamide.

* * * * *